United States Patent [19]

Piran et al.

[11] Patent Number: 5,445,936
[45] Date of Patent: Aug. 29, 1995

[54] METHOD FOR NON-COMPETITIVE BINDING ASSAYS

[75] Inventors: Uri Piran, Sharon; William J. Riordan, Boston; Laurie A. Livshin, Sharon, all of Mass.

[73] Assignee: Ciba Corning Diagnostics Corp., Medfield, Mass.

[21] Appl. No.: 121,806

[22] Filed: Sep. 15, 1993

[51] Int. Cl.[6] .............................................. C12Q 1/68
[52] U.S. Cl. ........................................ 435/6; 435/7.92; 435/7.94; 435/7.95; 436/518; 436/526; 436/527; 436/533; 436/534; 436/539
[58] Field of Search ................ 435/6, 7.92, 7.94, 7.95; 436/518, 539, 526, 527, 533, 534

[56] References Cited

U.S. PATENT DOCUMENTS

| | | | |
|---|---|---|---|
| 3,654,090 | 4/1972 | Schuura | 435/7.93 |
| 4,434,236 | 2/1984 | Freytag | 436/512 |
| 4,551,426 | 11/1985 | Freytag et al. | 435/7.92 |
| 4,670,383 | 6/1987 | Baier et al. | 435/7.92 |
| 4,788,136 | 11/1988 | Grenier et al. | 435/7.92 |

FOREIGN PATENT DOCUMENTS 139489 6/1985 European Pat. Off. .

OTHER PUBLICATIONS

Freytag, J. W. et al, 30:3, Clin. Chem. 417–420 (1984).
Hechemy, K. E. et al, Laboratory Management, 27 (Jun. 1984).
Jackson, T. M. et al., 87 J. Immuno Methods, 13–20 (1986).
Law, S. J., et al, 4, J. of Bioluminescence and Chemiluminescence, 88–98 (1989).
Leflar, C. C. et al., 30:11 Clin. Chem., 1809 (1984).
Miles, L. E. M. et al, 219 Nature, 186–189 (1968).
Piran, U. et al., 33/9 Clin. Chem. 1517–1520 (1987).
Piran, U. et al, 39/5 Clin. Chem. 879–883 (1993).
Weetall, H. 166 Science, 615–617, (1969).
Westall, H., et al., 185 Biochim. Biophys. Acta, 464–465 (1969).

*Primary Examiner*—Toni R. Scheiner
*Assistant Examiner*—Donna C. Wortman
*Attorney, Agent, or Firm*—Arthur S. Morgenstern; Nicholas I. Slepchuk, Jr.; Judith A. Roesler

[57] ABSTRACT

A novel non-competitive immunoassay technique has been developed which not only improves sensitivity, but also is convenient and less susceptible to interfering factors. It is compatible with existing instruments and is an assay that can be run in one test tube. The analyte is reacted with labeled specific binder, after which the mixture is reacted with (1) an insoluble material attached to an analyte derivative and (2) a solid phase carrying a binder. The solid phase is then separated, and the label attached to the solid phase is measured.

11 Claims, 9 Drawing Sheets

ADD
SAMPLE

ADD
TRACER

ADD
EXCESS
SOLID-PHASE
-ANALYTE MIMIC

SEPARATE
TRANSFER
SUPERNATE
TO A NEW CUVETTE

ADD SOLID
PHASE-ANTI-
TRACER

SEPARATE,
WASH, COUNT

HAPTEN (T3)

PROTEIN (TSH)

NUCLEIC ACID

| | COMPETITIVE FORMAT | | NON-COMPETITIVE FORMAT | |
|---|---|---|---|---|
| T3-ng/ml | RLU | NET/ZERO | RLU | NET/ZERO |
| 0 | 196041 | | 17049 | |
| 0.25 | 148660 | -0.24 | 54142 | 2.18 |
| 0.5 | 108908 | -0.44 | 86510 | 4.07 |
| 1 | 73347 | -0.63 | 124615 | 6.31 |
| 2 | 32211 | -0.84 | 191330 | 10.22 |
| 4 | 9847 | -0.95 | 251373 | 13.74 |
| 8 | 4313 | -0.98 | 288059 | 15.90 |

| | Capture with PMP-Goat Anti Mouse | | Capture with PMP-BgG-T3 | |
|---|---|---|---|---|
| T3, ng/ml | RLU | NET/ZERO | RLU | NET/ZERO |
| 0 | 52374 | | 7706 | |
| 0.25 | 76020 | 0.45 | 44589 | 4.79 |
| 0.5 | 94294 | 0.80 | 58081 | 6.54 |
| 1 | 122724 | 1.34 | 69083 | 7.96 |
| 2 | 151021 | 1.88 | 66570 | 7.64 |
| 4 | 180561 | 2.45 | 52796 | 5.85 |
| 8 | 194663 | 2.72 | 37825 | 3.91 |

METHOD FOR NON-COMPETITIVE BINDING ASSAYS

BACKGROUND

In developing a binding assay, it is important that the scientist develop one that has a high level of sensitivity and specificity, can eliminate interfering substances, and is convenient. The discussion herein may emphasize the immunochemical-type assay, but it should be recognized that the descriptions are also applicable to gene probe and other types of binding assays.

SENSITIVITY

Sensitivity means the minimal detectable dose, namely the smallest mass of analyte that generates a statistically significant change in the signal generated by the assay vs. that obtained in the absence of analyte. There is a need to increase sensitivity of binding assays (i.e., detect smaller amounts of analyte), because in many situations the analytes, whether they are hormones, drugs, microorganisms, toxins, pollutants or genetic materials, exert their effects at low concentrations. Furthermore, high sensitivity allows the use of small sample size, which can help to reduce "sample matrix" interferences. In addition, higher sensitivity allows measuring low analyte concentrations with a higher precision.

In discussing sensitivity, immunochemists have often distinguished between competitive assays and non-competitive assays. In a competitive assay, the signal which is measured is that emanating from the specific binder that does not bind analyte. For example, in some competitive assays, the labeled antibody is incubated with a sample containing analyte and a solid phase-immobilized analyte derivative. The labeled antibody that did not bind analyte binds the solid phase, and the signal emanating from the solid phase-bound labeled antibody is measured. In other types of competitive assays, unlabeled antibody is incubated with a sample containing an analyte and a labeled analyte derivative (or analyte mimic). The labeled analyte derivative binds those antibody binding sites that did not bind analyte. By measuring the signal coming from the labeled analyte derivative that bound the antibody, the assayist actually obtains an estimate of the concentration of antibody sites that did not bind analyte. Thus, in both types of competitive assays, one measures signal associated with the fraction of specific binder sites that did not bind analyte. The signal generated from a competitive assay decreases as the analyte concentration increases. Since small levels of analyte correspond to large signals, small changes in low concentrations of analyte lead to small differences between large numbers, which are hard to measure accurately.

A second type of binding assay is the non-competitive type. In this assay, a labeled specific binder, for example a labeled antibody, is incubated with the sample and binds a portion of the analyte. In one variation (type A) of non-competitive assay, a solid-phase immobilized unlabeled specific binder is added, simultaneously or in sequence, to bind another epitope on the analyte, in which case it is called a "sandwich" assay. For example, the immobilized molecule might be an antibody against a second epitope on the analyte, and the analyte might form a ternary complex with the labeled antibody and an immobilized unlabeled antibody. The solid phase is then washed and the signal measured is the signal that comes from the ternary complex containing the analyte. In this case the signal increases with increasing analyte concentration.

Another variation of the non-competitive immunoassay (type B) was invented by L. E. M Miles and C. N. Hales, Nature 219:186, 1968. In this type of assay the labeled antibody is first incubated with the analyte to form an immune complex, and then the mixture is contacted with a solid phase. This solid phase has an analyte derivative (or mimic) in large excess, which causes the unreacted labeled antibody to bind to it. The solid phase is then separated from the liquid phase and a portion of the liquid phase is taken for signal measurement. The difference from the competitive type of assay is that one does not measure the signal associated with the solid phase, namely the labeled binder that did not bind analyte. What one measures, instead, is the signal associated with the labeled binder that bound analyte and consequently did not bind the immobilized binder, thus remaining in the liquid phase.

Type A of the non-competitive assay has the potential for the highest sensitivity. Jackson and Ekins (T. M. Jackson and Ekins, R. P., Journal of Immunological Methods, 87:13, 1986) showed by mathematical analysis that when the specific activity of the label is not limiting, the sensitivity of type A is higher than that of the competitive assay. Empirical data supports the conclusion that type A of immunoassays is more sensitive than the competitive type of immunoassays: several immunoassays, such as thyroid stimulating hormone, have sensitivity of several million molecules per assay cuvette; in contrast, the most sensitive competitive immunoassays, such as those of digoxin and triiodothyronine, have sensitivities of several billion molecules per assay cuvette. Although type A assays are the most sensitive type, there is a need to improve their sensitivities even further.

The large gap in potential sensitivity (a number of orders of magnitudes, depending on the value for fractional non-specific binding) between the competitive type and type A of the non-competitive is the main reason for the wide use of type A. The former is used either when high sensitivity is not required or when type A is not possible due to the existence of only one epitope on the analyte, as is the case for analytes that are haptens or short peptides.

Theoretical considerations, first advanced by Miles and Hales, strongly suggest that the type B non-competitive assay, suitable for analytes with one epitope, should also allow higher sensitivity than the competitive type. This is because the formula for calculating sensitivity of type A (see Jackson and Ekins, 1986) can be applied if we replace "Fractional non-specific binding" with its equivalent "Fractional non-specific retention". This latter term is simply the concentration of the unreacted labeled binder that failed to separate from the labeled binder-analyte complex in the liquid phase, much the same as the non-specific binding refers to the unreacted labeled binder that failed to separate from the complex on the solid phase.

Thus, from a mathematical standpoint, the non-competitive assay should be more sensitive. The signal increases as the concentration of analyte increases, and low concentrations of analyte can be detected more easily since small differences between small numbers are relatively easy to distinguish, and the signal due to the presence of analyte is distinguished from a small, rather than a large background.

Thus, theory predicts that type B assays have a potential for a substantially higher sensitivity than competitive assays. Furthermore, if the non-specific retention of labeled binder is on the same order of magnitude of non-specific binding and given the same assay conditions (including antibody affinity, incubation time, separation time, etc.), sensitivities of types A and B should be similar. Subsequent reports on the use of this assay method are: Schuurs and Van Weemen 1972, U.S. Pat. No. 3,654,090; Freytag et al. 1984, Clin. Chem. 30:417; Leflar et al. 1984, Clin. Chem. 30:1809; Freytag 1984, U.S. Pat. No. 4,434,236; Freytag et al. 1985, U.S. Pat. No. 4,551,426; Baier et al. 1987, U.S. Pat. No. 4,670,383; Grenier et al. 1988, U.S. Pat. No. 4,788,136. These reports claim high sensitivity, but direct comparison to the competitive assay type is not presented. One may speculate that the theoretical expectation will not be fulfilled if the fractional non-specific retention is not sufficiently low or that during the separation steps a portion of the complex composed of labeled specific binder-analyte is lost due to dissociation reaction. All of these factors will reduce sensitivity, and attempts to lower the non-specific retention, by increasing concentration of the solid phase or the incubation time with the solid phase, unfortunately tend to lead to more dissociation and, thereby, a loss of the complex labeled specific binder-analyte.

Baier et al. described a non-competitive immunoassay format of type B with an added separation step. (See FIG. 1 for Baier analytical procedure.) After incubating the sample containing analyte with the labeled antibody, a solid phase with immobilized analyte derivative is added to bind the unreacted labeled antibody. The solid phase is separated and an aliquot of the remaining liquid phase is pipetted off to a new reaction cuvette containing a second solid phase. The second solid phase has an immobilized antibody against the labeled antibody or some part of the labeled antibody-analyte complex. The signal associated with the complex captured on the second solid phase is measured. The intent of this additional step was to allow a wash step in order to remove sample matrix interfering factors. It is not clear whether a substantial improvement of sensitivity was achieved by this additional step, because comparison to the competitive version of the same assay is not presented by Baier et al. Since competitive solid phase assays include one separation step, the added inconvenience of two separation steps in the Baier et al. patent is a disadvantage. This may be the main reason for which the method has not been commercialized or widely used in academic settings.

Baier avoids mixing of the two solid phases because he could not separate them later, and even if he used separable solid phases, it was believed that the two solid phases would clump together, since they carry immunochemical binding partners (anti-label on one particle is a binding partner with a labeled antibody bound to the other particle). Clumping of particulate solid phases coupled to immunochemical binding partners is used often in particle agglutination assays. (See K. E. Hechemy and E. E. Michaelson, Laboratory Management, June, 1984, pp. 27–40.)

Our finding that both solid phases can be retained in the same reaction tube is a novel and significantly important aspect of the instant invention. This allows the use of the currently existing instruments and doesn't require a more complex mechanism that would incorporate the separation of the second solid phase.

ELIMINATION OF INTERFERING SUBSTANCES

Often the sample to be analyzed in an immunoassay is delivered in an environment that includes interfering substances. For example, a serum sample not only contains the analyte of interest, but also many components that could interfere with the immunoassay. Immunochemical assay techniques include steps that easily isolate the analyte from the interfering substances. For example, the analyte can be reacted with an antibody which is connected to a solid phase. The solid phase can then be separated from the other components in its environment and analyzed.

The separation step referred to above can be accomplished in one of many ways. For example: an assayist can use nonmagnetic particles as the solid phase using either centrifugation filtration as the method of separation, or magnetic particles as the solid phase, in which case the separation is accomplished by the application of a magnetic field. Other effective means of separation involve various chromatographies, electrophoreses, and the use of extended surfaces, such as microtiter plates, large beads, fibers and others. The separation step can be done manually or by an automated or non-automated instrument; in either case, however, the solid phase is separated and washed, the liquid phases are discarded, and the solid phase-associated signal is the one being measured.

Many substances interfere with the assays despite the wash steps. For example, cross-reactants share structural similarities with the analyte and also bind the labeled or unlabeled specific binder. When a cross-reactant binds the labeled specific binder the assay result is falsely elevated. When sufficiently high concentration of a cross-reactant binds the unlabeled specific binder and saturate it, a falsely low result is obtained.

Occasionally the analyte itself is present in an extremely high concentration and thereby saturates the unlabeled specific binder, leading to a "high dose hook effect".

Heterophilic antibodies and rheumatoid factors bind antibodies and can either form a bridge between the labeled and unlabeled antibodies or inhibit their desired binding activity, leading to false results.

CONVENIENCE

Whether it is done manually or by an automated instrument, the separation step is one of the most technically demanding operations in the assay. It needs to be done rapidly, so that the analyte-binder complex of interest does not dissociate. It also needs to be efficient, so that the unbound labeled binder and interfering substances are nearly completely removed. In addition, it needs to be reproducible, in order to maintain overall high assay precision. These demands on the separation step are the impetus for the development of the various "homogeneous", or "no-separation" assays, where there is no separation of the solid phase. It is clear from this discussion that the Baier technique, by employing an additional separation step is disadvantageous in this respect. The extra separation step of the Baier technique is especially complicated and problematic, since it requires an additional reaction vessel for each sample tested. Furthermore, no commercial automated instruments exist today that can perform the transfer of the liquid phase to a second reaction vessel containing a second solid phase. Performing the step manually is extremely tedious and difficult to do reproducibly.

Given the present level in sophistication in immunoassay techniques, to be considered convenient an assay should not require additional steps beyond what is currently used on a given instrument (i.e., there should not be a need to retrofit the instrument). Furthermore, the assay should preferably be capable of being run in one tube.

SUMMARY OF THE INVENTION

A novel non-competitive immunoassay technique has been developed which not only improves sensitivity, but also is convenient and less susceptible to interfering factors. It is compatible with existing instruments and is an assay that can be run in one test tube. The analyte is reacted with labeled specific binder, after which the mixture is reacted with (1) an insoluble material attached to an analyte derivative and (2) a solid phase carrying a binder. The solid phase is then separated, and the label attached to the solid phase is measured.

DETAILED DESCRIPTION OF THE INVENTION

Figure 1:
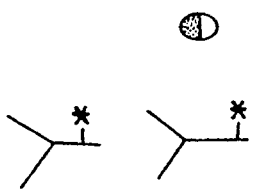
FIG. 1 illustrates a scheme for the assay technique of Baier et al.
Figure 1:
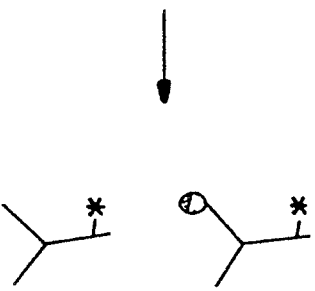
Figure 1:
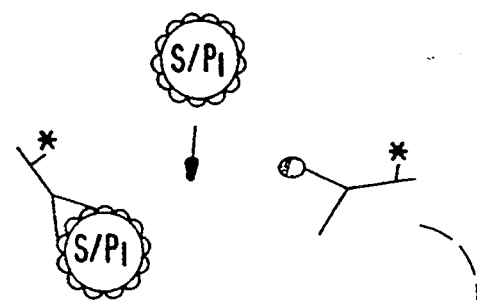
Figure 1:
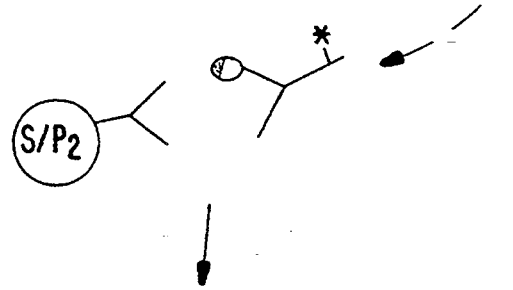
Figure 1:
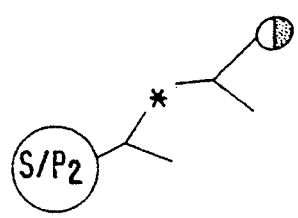

A convenient binding assay technique that has improved sensitivity and is less susceptible to interfering substances is described herein. One of its primary applications is in the field of immunochemistry, and, thus, most of the discussion of the technique is related to the immunochemistry field. However, it should be noted that the technique is equally applicable to other binding assays, such as gene probe assays and receptor assays. This assay technique is suitable for a wide diversity of analytes, including those with one or more epitopes. Analytes may include proteins, peptides, drugs, hormones, environmental pollutants, nucleic acids, lipids, carbohydrates and various conjugates of these. The technique is suitable for both determination of the total amount of analyte in the sample or the free fraction (e.g. free hormones and free drugs in biological fluids).

The sample suspected of containing analyte is incubated with Reagent 1, which comprises a labeled specific binder that binds at least a portion of the analyte. After allowing for an incubation period for the analyte and labeled specific binder to react with each other, two additional reagents are then added, either simultaneously (reagents 2 and 3 are pre-mixed) or sequentially (reagent 2 is added first and reagent 3 is added later).

Many types of labels have been used in binding assays, for example radiochemical, luminescent, fluorescent, chemiluminescent, enzymatic, liposomal and various metal and non-metal particles. Preferably, the label is a chemiluminescent label (e.g., an acridinium ester) or an enzymatic label. The label can be attached directly to the specific binder by a covalent bond. Alternatively it can be attached indirectly using a binding pair such as biotin/avidin, DNP/anti-DNP or any other binding pair. All are similarly suitable for use in the assays described herein.

Reagent 2 contains a component comprising an analyte or analyte derivative or analyte mimic attached to an insoluble material that retards or reduces the binding of the previously unreacted labeled specific binder to reagent 3. If it did not reduce this binding, the binder attached to reagent 3 might bind not only to the labeled binder-analyte complex, as desired, but also to the labeled binder which is now bound to the insoluble material, thereby increasing the non-specific signal. In most cases reagent 2 retards binding due to its steric hindrance, and examples of this insoluble material include particles made of controlled-pore glass, polymer particles, latex, colloidal metal or metal oxide particles, immiscible liquid phase, extended surface, porous paper, porous gel, liposome, emulsion, a system of very small particles that do not settle readily by standing or centrifugation, paramagnetic particles, cellulose beads, cross-linked dextran or any other particle. Extended surface is meant to include relatively flat surfaces, such as the surface of a cuvette or a microtiter plate, and the surface of a relatively large bead, such as one with diameter of greater than 1 mm. Preferred insoluble materials are controlled pore glass, polymer particles, latex particles, cross-linked dextran and extended surfaces. Particle size can vary from 10 nm to several microns in diameter, and smaller materials may include large molecular polymers such as dextran or protein aggregates. Larger beads of any size, flat surfaces, testtube wall, dipstick surface, fibers, membranes, rods and discs, or any extended or particulate surface capable of carrying an immobilized binder can also be used. Other mechanisms aside from steric hindrance (for example, porosity) also tend to retard the binding to reagent 3.

Although reagent 2 can be in the form of particles or an extended surface, it does not function as usual solid phases function in binding assays, because there is no need to separate reagent 2 from the liquid phase containing the sample and other components of the assay. However, reagent 2 should not substantially adhere to the solid phase or be co-separated with it. Therefore, if the solid phase is separated from the liquid phase containing the sample plus other assay components prior to signal measurement, reagent 2 should remain substantially with the liquid phase and be removed together with it. For these reasons and to distinguish it from a true solid phase, the material used in reagent 2 is referred to as insoluble material.

The component attached to the insoluble material in reagent 2 can be an analyte or a derivative of the analyte. Thus the affinity of the labeled specific binder to this component may be similar (within the same order of magnitude) to its affinity toward the intact analyte. Alternatively, the component may be an analog of the analyte, the affinity of which to the labeled specific binder being much lower (by more than one order of magnitude), in this case the binding of the labeled specific binder to reagent 2 is facilitated by avidity (cooperativity between two or more binding site of the binder. See Piran U. et al. Clinical Chemistry Vol. 39, pp. 879–883, 1993). The component may be a synthetic molecule (such as an organic molecule, a synthetic peptide or an oligonucleotide) or a biologically derived molecule (such as a protein, a peptide, an antibody, an antiidiotypic antibody, receptor, antigen, nucleic acid etc.).

Reagent 3 is a solid phase containing an immobilized binder that binds the labeled specific binder-analyte complex. This immobilized binder can be an antibody against (1) the specific binder, (2) the label, or (3) the complex. Alternatively, the immobilized binder can be, in the case when bi- or multi- valent labeled specific binder is used, an analyte or analyte mimic. Furthermore, when the analyte is bi- or multi-valent, the immobilized binder can be an anti-analyte, a specific receptor, or a complementary nucleic acid sequence. In other words, it can bind with any portion of the labeled specific binder-analyte complex. After addition of reagents 2 and 3, the incubation continues in order to bind the labeled specific binder-analyte complex to reagent 3. Finally, the signal emanating from the label associated with the solid phase (reagent 3) is measured. Prior to this signal measurement, the solid phase may be separated and washed, but in the cases of sensors or pseudohomogeneous assays, separation is not necessary.

Solid phase materials may include: paramagnetic particles, particles made of controlled-pore glass, polymer particles, latex, colloidal metal or metal oxide particles, immiscible liquid phase, extended surface, porous paper, porous gel, lipos cellulose beads, cross-linked dextran or any other particle. Particle size can vary from 10 nm to several microns in diameter, larger beads of any size, flat surfaces, testtube wall, dipstick surface, fibers, membranes, rods and discs, or any extended or particulate surface capable of carrying an immobilized binder. Preferably, the solid phase material is either a paramagnetic particle or an extended surface.

Various techniques can be used for separation of the solid phase from the liquid phase, including centrifugation, filtration, settling by gravity, magnetic attraction, electrophoresis, various column chromatographies, capillary forces, etc. The present invention is also compatible with the sensor format, which does not requires removal of the liquid phase, since the sensor can read the signal that is situated near the sensor surface, with only small amount of liquid phase signal being read by the sensor. Also compatible are both batch systems such as those used in automated laboratory instruments, and continuous flow systems Assay formats involved in "near patient testing," such as dipsticks, immunochromatography and immunoconcentration devices are compatible with the present invention.

This novel procedure can be utilized with analytes having one epitope as well as analytes with two or more epitopes, and examples demonstrating variations in the scheme are shown below. In addition, this analytical technique can be used for procedures aside from immunoassays, such as gene probe and receptor assays.

Figure 2:
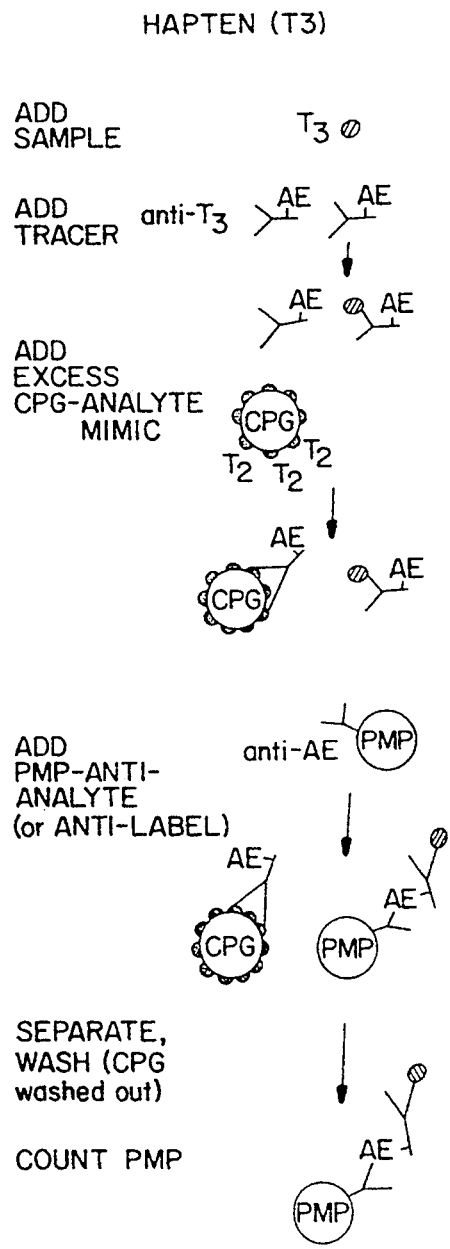
FIGS. 2-4 illustrate schemes for assay formats according to the present invention, with FIG. 2 illustrating a monoepitopic example, FIG. 3 showing a sandwich type with at least 2 epitopes, and FIG. 4 illustrating a gene probe assay.

FIG. 2 illustrates the novel procedure as it applies to a monoepitopic analyte (triiodothyronine, T3). Because there is only one epitope on the analyte, the binder attached to the second solid phase cannot be an anti-analyte, but a binder of any part of the labeled anti-T3; in this case it is an anti-label. This solid phase is a universal reagent that can be used for assays of a wide variety of analytes. (See Example 1.)

Figure 3:
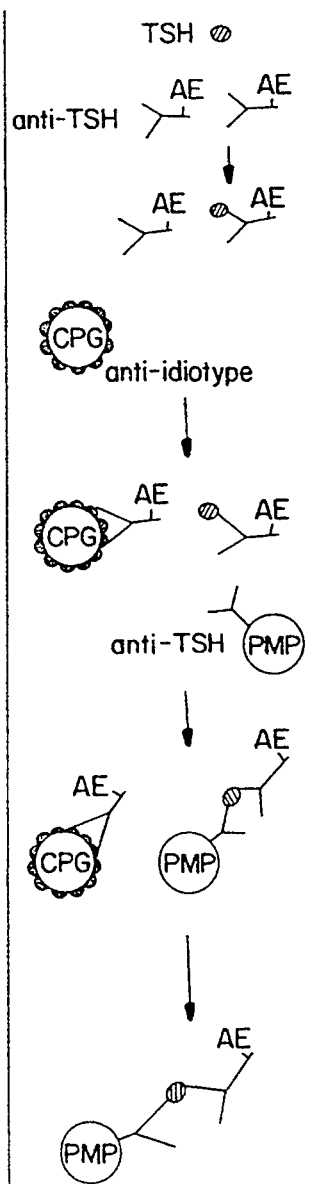

FIG. 3 illustrates the procedure for an analyte which has at least 2 epitopes (thyroid stimulating hormone or TSH). With this analyte, it is feasible to use a solid phase binder that binds directly to the analyte, such as an anti-TSH. However, it is also feasible to use an anti-label or a binder to any other part of the labeled specific binder. This may be instrumental in avoiding deleterious effect of cross-reactants, interfering substances or a very high analyte concentration, that otherwise would exert their effect on the immobilized analyte. (See Example 4.)

Figure 4:
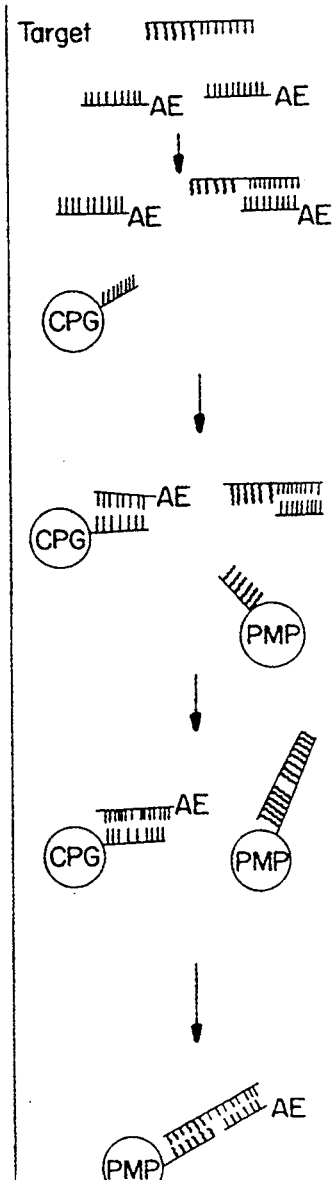

FIG. 4 illustrates a similar reaction mechanism with a gene probe assay. Because nucleic acids are polymers of high molecular weight, the solid phase binder can usually be a sequence complementary to the target analyte, which will be referred to as an epitope, as shown in FIG. 4. However, as in the case of immunoassays for multi-epitopic analytes, in some cases it may be advantageous to use an anti-label.

Sample interferences in the instant invention can be reduced by using a smaller sample volume and eliminated by avoiding the use of a binder to a second epitope. (I.e., increased interference is encountered when the sample contains (1) an excess of analyte, which may cause a "hook effect", or (2) a molecule that cross reacts with the binder to the second epitope.) In addition, applicant has surprisingly found that materials that are similar to the analyte in their chemical structure (e.g., cross-reactants) exert a smaller effect on the signal of the novel assay method than on the conventional competitive method. (See Examples 1 and 3.)

This procedure is compatible with currently existing automated immunoassay instruments and, thus, can be utilized on them without the need to redesign the instruments. The procedure is also convenient for using manually or on non-automated instruments.

The following examples illustrate the procedure of this invention.

EXAMPLES

Example 1. Total triiodothyronine (T3) assay

REAGENTS

Monoclonal anti-T3 and anti-DMAE antibodies were produced in mice (A/J) by immunizations and subsequent fusions of the splenocytes with Sp2/0-Ag 14 myeloma cells by the procedure described by Kohler and Milstein in Nature (London) Vol. 256, pp. 494–497 (1975). The immunogen for producing anti-T3 was bovine-serum albumin (BSA-T3), prepared as described by Burke and Shakespear in J. Endocrinol. Vol. 65, p. 133 (1975). The immunogen for producing anti-DMAE was Keyhole Limpet Haemocyanin KLH-DMAE, prepared with an input ratio of 500:1 DMAE per protein as described by Law et al. in J. Biolumin. Chemilumin. Vol. 4, pp. 88–98 (1989). Mice were immunized 3 times with about 0.1 mg immunogen. The first injection was in Complete Freund's Adjuvant and subsequent ones in Incomplete Freund's Adjuvant. Four days prior to the fusion, mice were immunized with 0.01 mg of antigen intraveneously. Spleen cells from immunized mice were fused with myeloma cells at a ratio of 5:1. Cell culture supernatants were screened for antibody activity production 7–21 days post fusion, when macroscopic colonies were observed. The tracers used for screening for anti-T3 and anti-DMAE antibodies were I-125-T3 and DMAE, respectively, and the solid phase was PMP-goat-anti-mouse-IgG. Hybridoma cells secreting the desired antibodies were injected intraperitoneally into pristane-primed mice (CAF).Ascitic fluids from these mice were collected after 3–5 weeks. The antibodies were purified from the ascitic fluid by Protein A column chromatography using Affi-gel Protein A MAPS II kit (Bio-Rad Laboratories, Richmond, Calif. 94901) according to the protocol provided with the kit.

Bovine gamma globulin (BGG) was coupled to N-hydroxysuccinimide activated N-hemisuccinate methyl esters of L-T3 and L-3,5-diiodothyronine (T2) as described for L-thyroxine by Law et al in J. Biolumin. chemilumin. Vol. 4, pp. 88–98 (1989). BGG-T2 was coupled to CNBr-activated Sepharose 6B (Pharmacia, Piscataway, N.J.) and used for affinity purification of anti-T3 according to the manufacturer's instructions.

Paramagnetic particles (PMP) coupled to BGG-T2 or BGG-T3 or anti-DMAE were prepared as described by Groman et al. BioTechniques, Vol. 3, pp. 156–160 (1985). BGG-T2 was coupled to controlled pore glass (CPG) particles by essentially the same method described therein. The CPG itself (same material used in Ciba Corning's Immophase products; 1 micron diameter; has aminosilane groups on its surface) was prepared essentially as described by H. H. Weetall. (See Science, 166:615, 1969; Nature, 223:959, 1969; Biochim and Biophys Acta 185:464, 1969.)

The protein A purified anti-T3 and anti-DMAE and affinity purified anti-T3 were labeled with DMAE as described by Law et al in J. Biolumin. Chemilumin. Vol. 4, pp. 88–98 (1989).

ASSAYS

Figure 5A:
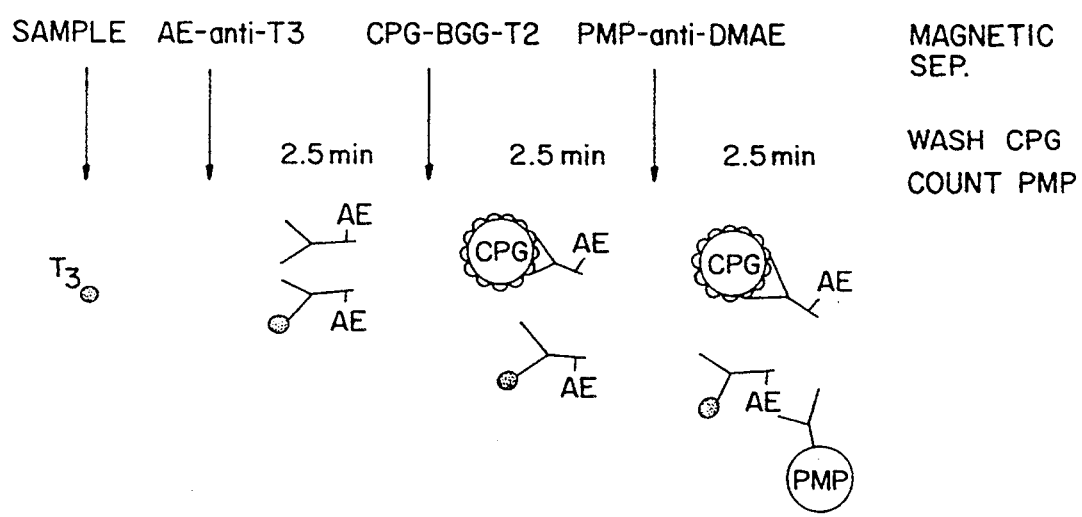
FIG. 5A illustrates a non-competitive T3 assay utilizing the present invention.

The non-competitive assay of T3 was performed on the ACS:180 instrument (Ciba Corning Diagnostics Corp.). The sample probe delivered 0.01 ml sample or standard and 0.05 ml 0.15N NaOH to the reaction cuvette. Reagent probe 1 delivered 0.1 ml affinity purified, DMAE-labeled anti-T3, 2X10e6 relative light units (RLU) in Buffer A containing 140 mM sodium phosphate, 20 mM sodium barbital, 4 mM sodium chloride, 1 mM ethylenediamine-tetraacetic acid (EDTA), 0.15 g/L 8-anilino-1-naphtalene-sulfonic acid (ANS), 1 g/L sodium azide, 0.02 g/L bovine gamma globulin (BGG), and 2.5 g/L bovine serum albumin (BSA), pH 6.6. After 2.5 min incubation at 37C reagent probe 2 delivered 0.1 ml of CPG-BGG-T2 in Buffer B containing 50 mM sodium phosphate, 150 mM sodium chloride, 1 mM EDTA, 0.2 g/L sodium azide, and 1 g/L BSA, pH 7.4. After an additional 2.5 min incubation reagent probe 3 delivered 0.05 mg of PMP-anti-DMAE in 0.5 ml Buffer B. Following another 2.5 min incubation the instrument attracted the PMP to the cuvette wall and performed two washes with 1 ml dionized water. The instrument then added 0.3 ml of 5%(v/v) H2O2 in 0.1N HNO3 and 0.3 ml of 0.1N NaOH, 0.5% (w/V) cationic surfactant Arquad, and the light was collected in the instrument's photomultiplier tube and was expressed as RLU's. (See FIG. 5A for a scheme of the reaction).

Figure 5B:
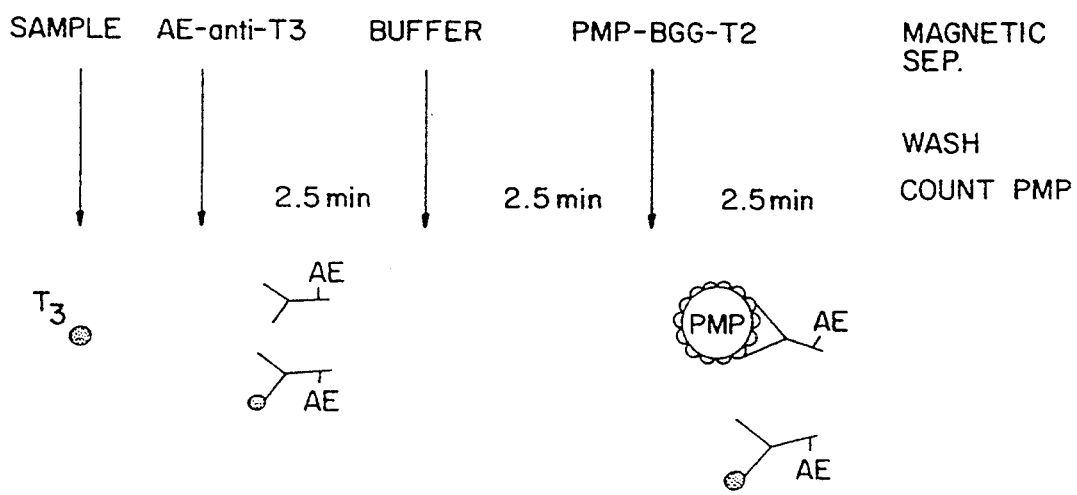
FIG. 5B illustrates a competitive T3 assay, both run on an automated immunoassay instrument.

The competitive assay of T3 was performed on the same instrument under similar conditions. The sample probe delivered 0.01 ml sample or standard and 0.05 ml of 0.1N NaOH to the reaction cuvette. Reagent probe 1 delivered 0.1 ml of the same DMAE-labeled anti-T3 as in the case of the non-competitive assay. After 2.5 min incubation reagent probe 2 added 0.1 ml of buffer, and after another 2.5 min reagent probe 3 delivered 0.005 mg of PMP-BGG-T2 in 0.5 ml of Buffer B (See FIG. 5B for a scheme of the reaction). Separation and washes of the PMP and light measurement was done by the instrument under the same conditions as for the non-competitive assay. Both types of assays were run in triplicates.

Figure 6:
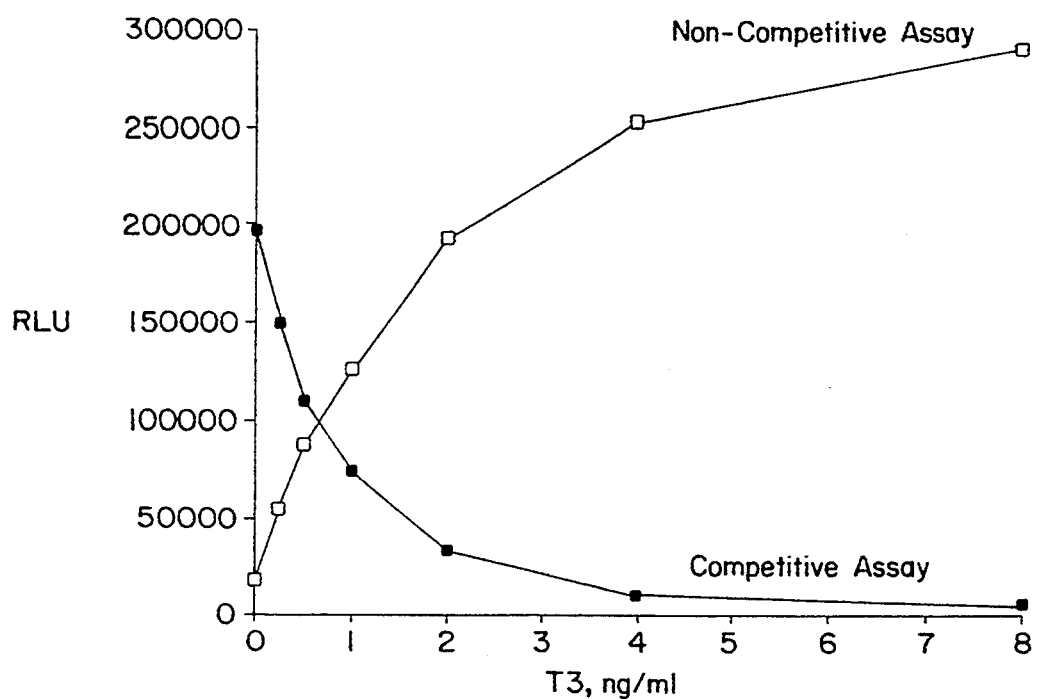
FIGS. 6-8 illustrate the results from the assays for monoepitopic analytes as described in the Examples.

The standard curves obtained in the two types of assays is shown in FIG. 6. The change in signal caused by the lowest standard (0.25 ng/ml) as a fraction of the signal at zero T3 is about 9-fold larger in the non-competitive than the competitive assays. When the precision of the signal is the same in both assays, these results predict about 9-fold increased sensitivity, namely 9-fold decreased minimal detectable dose. The signal precision was indeed found to be identical by testing 50 repetitions of a serum standard containing 0.15 ng/ml. The competitive assay gave signal coefficient of variation (CV) of 2.1% and the non-competitive assay gave CV of 1.9%. In addition, nearly identical signal CV's were found in both assays at all levels of T3. Serial dilutions of the lowest standard and subsequent replicate (n=10) determinations showed that in the competitive assay the 0.0625 ng/ml standard was detectable, since it was the lowest dose outside the 3 standard deviations from the zero-dose signal. By the same criterion, the non-competitive assay was able to detect 0.0078 ng/ml. When serum samples ranging between 0.2–3.4 ng/ml T3 from 47 human subjects were tested in the two methods, the two methods were in close agreement: the correlation coefficient was 0.995, slope of the regression line was 1.02 and the intercept was $-0.04$.

Surprisingly, cross-reactivity in the non-competitive assay of 3,5-T2 was 7.5-fold lower (0.02% vs. 0.15%) and the cross-reactivity of reverse-T3 was twofold lower (0.15% vs 0.07%) than in the competitive assay.

Figure 7:
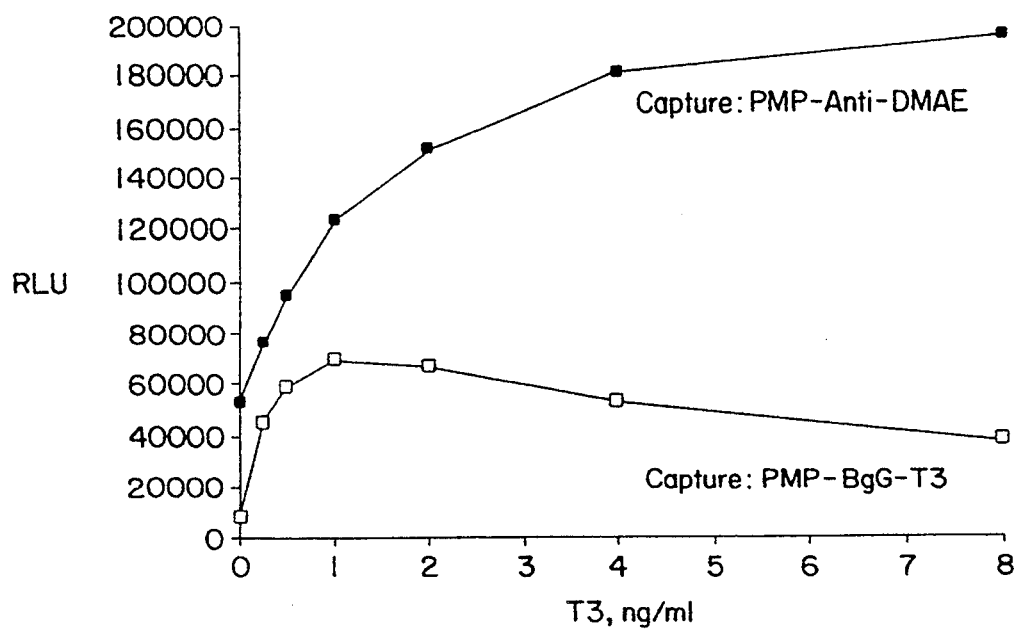

Replacing the DMAE-labeled affinity purified anti-T3 with a DMAE-labeled protein A purified antibody led to a tenfold increase in zero-dose signal in the non-competitive assay. This was caused by the presence of labeled anti-T3 that is denatured or otherwise unable to bind the immobilized ligand. This could be overcome by using PMP-BGG-T3 instead of PMP-anti-DMAE (see FIG. 7). A combination of affinity purified tracer and PMP-BGG-T3 gave the lowest "NSB", and therefore had the potential for the highest sensitivity. There was little change in the competitive assay when the tracer was not affinity purified.

Example 2. Free T3 assay

The free T3 assay was performed on the ACS:180 using the same reagents and protocol as used in Example 1, except that Buffer B was used in all reagents.

The standard curve of the non-competitive assay showed about 8.5-fold higher sensitivity than the competitive one. Results from 47 samples showed close agreement between the methods (R=0.95, slope=0.88, int=$-0.13$).

Example 3. Digoxin assay

A monoclonal anti-digoxin antibody was obtained from Chemicon International, Inc., Temecula, Calif. Digitoxin was coupled to BGG by the periodate method described by Butler and Tse-eng in Methods in Enzymology, Vol. 84, pp. 558–577 (1982). The methods described in Example 1 were used to affinity purify the antibody on Sepharose-BGG-digitoxin, immobilize BGG-digitoxin on CPG and PMP and to label the purified antibody with DMAE.

Three types of immunoassays of digoxin were performed.

For the non-competitive assay of the present invention 0.05 ml of standards and 0.05 ml DMAE-labeled affinity purified anti-digoxin 2X10e6 RLU's in Buffer C containing per liter: 8.5 g sodium chloride, 1 g sodium azide, 6.66 g Tris base, 0.38 EDTA, 5 g BSA and 5 g BGG at pH 7.8. The standards and tracer were mixed in a 12×75 mm polystyrene test tubes and incubated in for 10 min at 37C. One mg of CPG-BGG-digitoxin in Buffer B was then added, mixed and the mixture was incubated for 10 min at 37C. PMP-goat-anti-mouse-IgG (Advanced Magnetic Corp., Boston Mass.), 0.05 mg in Buffer B was added to capture the labeled antibody-analyte complex for 10 min. The tubes were then placed in a magnetic separators, the PMP was washed twice with deionized water and the chemiluminescence associated with the PMP was measured in a luminometer (Magic Lite Analyzer II, Ciba-Corning Diagnostics Corp.) as described by Piran et al. in Clinical Chemistry Vol. 33, pp. 1517–1520 (1987).

For the competitive assay the CPG-BGG-digitoxin was replaced by the buffer alone and the PMP-goat-anti-mouse-IgG was replaced by PMP-BGG-digitoxin.

Figure 8:
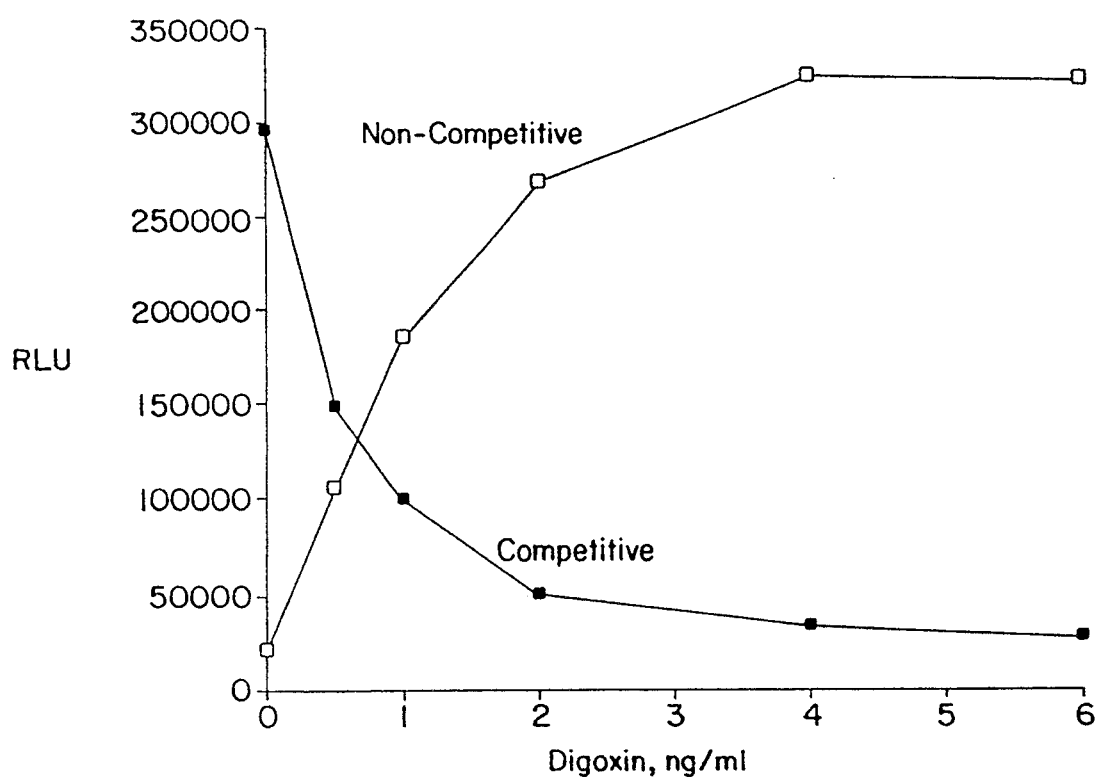

The standard curves for the non-competitive assay of the present invention and the competitive assay are shown in FIG. 8. It can be seen that the non-competitive assay is about 8-fold more sensitive than the competitive one, based on the change of signal as a fraction of the zero-dose signal. Serial dilutions of a digitoxin solution showed the non-competitive assay to give 10-fold less cross-reactivity with digitoxin than the competitive one (0.05% vs. 0.5%).

Figure 9:
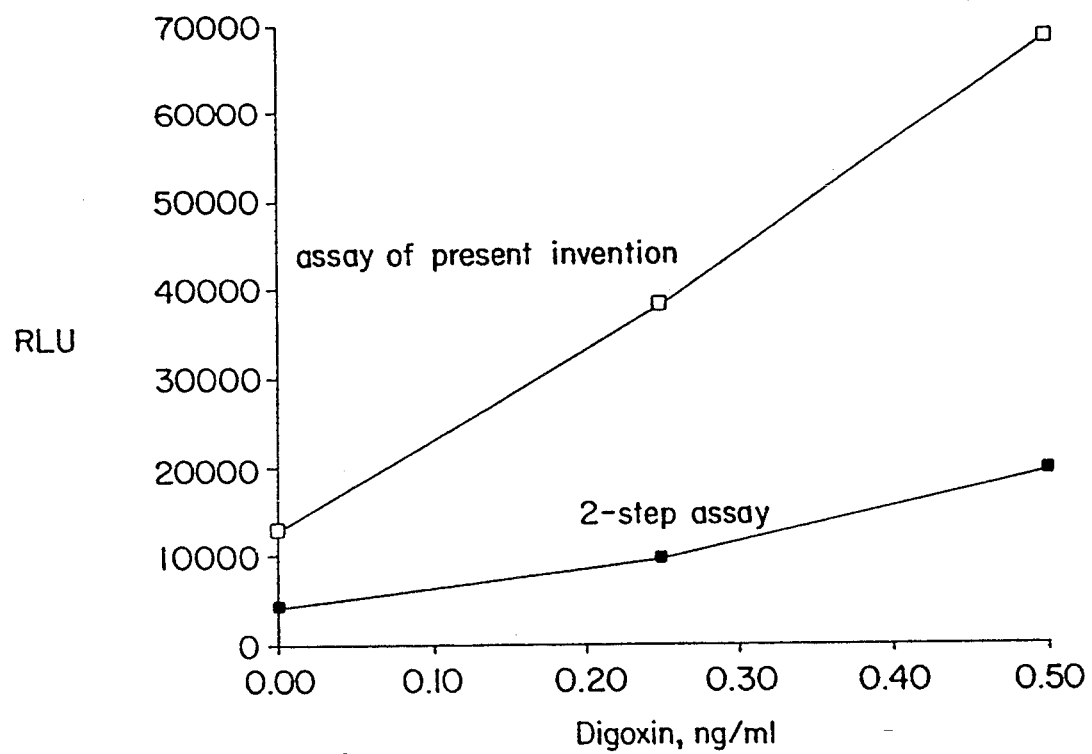
FIG. 9 shows a comparison to the results of using the novel assay technique vs. the technique of Baier et al.

A third type of digoxin assay was performed essentially as described by Baier et al.. After incubating the 0.025 ml of the standards and 0.05 ml of the labeled antibody for 1 hour at room temperature (RT), 0.25 mg CPG-digitoxin in 0.1 ml was added and the mixture incubated for 5 min. The test tubes were spun for 10 min in a clinical centrifuge at 2000 revolutions per minutes and 0.1 ml of the clear supernatant was aspirated with a pipet and transferred to a new test tube. To the second tube was added 0.05 mg of PMP-anti-DMAE in 0.5 ml and the mixture incubated for 30 min at RT. All reagents were in Buffer B. Further processing and light measurements were done as in the first two digoxin assays. For comparison to the non-competitive assay of the present invention a duplicate assay was run simultaneously that was identical up to the centrifugation step. The centrifugation was omitted and 0.05 mg PMP-anti-DMAE was added and incubation was continued for another 30 min. Further processing and readout were done as in the other versions of digoxin assay. The resulting standard curves of the two types of non-competitive assays are shown in FIG. 9. It is clear that the curve obtained by the Baier et al. version gives lower signal throughout. The results can be at least partially explained by the transfer of 0.1 ml out of a total of 0.175 ml of incubation mixture. This was done in order to avoid disturbing the sediment, which would cause the transferring of CPG to the second test tube, leading to loss of sensitivity.

Example 4. Thyroid stimulating hormone (TSH) assay

Monoclonal anti-TSH antibodies (7A10 and 11A8) were prepared by immunizations of mice (Balb/c) with human TSH essentially by the methods described in Example 1. An antiidiotypic anti-anti-TSH (7A10) was produced by immunizing mice (A.SW) with Fab2 fragments of anti-TSH (7A10) coupled to maleimide-activated keyhole limphet heamocyanine (Pierce Chemical Co.). The Fab2 fragments were prepared by digestion with pepsin as described in "Antibodies: a laboratory manual" E. D. Harlow and D. Lane Eds. Cold Spring Harbor Pub. 1988, pp. 630–1. Screening for anti-TSH antibodies was done with I-125-TSH and PMP-goat-anti-mouse-IgG. For screening the antiidiotype producing cells, PMP-anti-TSH (7A10) and DMAE-anti-TSH (7A10) were incubated with cell culture supernatants and the presence of antiidiotype was detected by formation of a bridge between the PMP and the label. Inhibition of the bridge formation by TSH was used to confirm the specificity of the antiidioype. Anti-TSH (7A10) was labeled with DMAE, and anti-TSH (11A8) and antiidiotype anti-anti-TSH (7A10) were immobilized on PMP and CPG, respectively as described in Example 1.

Figure 10A:
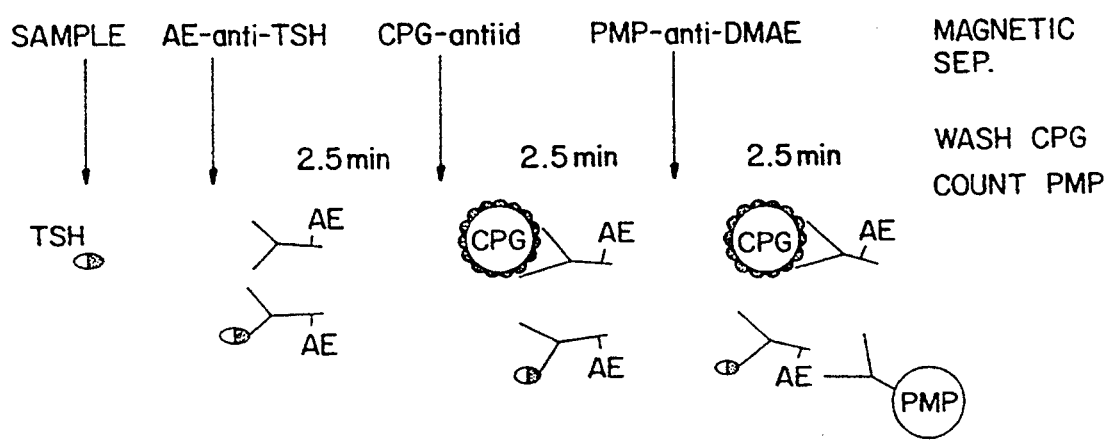
FIG. 10A shows a scheme of the non-competitive assay of the present invention as applied to a protein analyte (TSH) possessing more than one epitope using a solid phase immobilized anti-label.
Figure 10B:
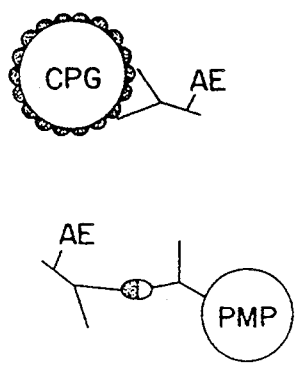
FIG. 10B shows use of a solid phase immobilized anti-analyte in an assay that is otherwise the same as FIG. 10A.

The TSH assay was performed on the ACS:180 instrument. The sample probe added 0.1 ml standard to the reaction cuvette. Reagent probe 1 added 0.1 ml DMAE-anti-TSH (7A10) 2X10e7 RLU's in Buffer B. After 2.5 min incubation at 37C reagent probe 2 added 0.1 ml 0.2 mg CPG-antiidiotype (anti-11A10) in Buffer B. After 2.5 min incubation at 37C reagent probe 3 added 0.25 ml of 0.05 mg PMP-anti-DMAE or PMP-anti-TSH (11A8) in Buffer B. Following 2.5 min incubation at 37C, magnetic separations and two washes with deionized water, the chemiluminescence associated with the PMP's was measured by the instrument. The mechanism of the two assays using PMP-anti-DMAE (i.e., the antibody against the labeled antibody) and PMP-anti-TSH are depicted in FIGS. 10A and 10B, respectively.

Figure 11:
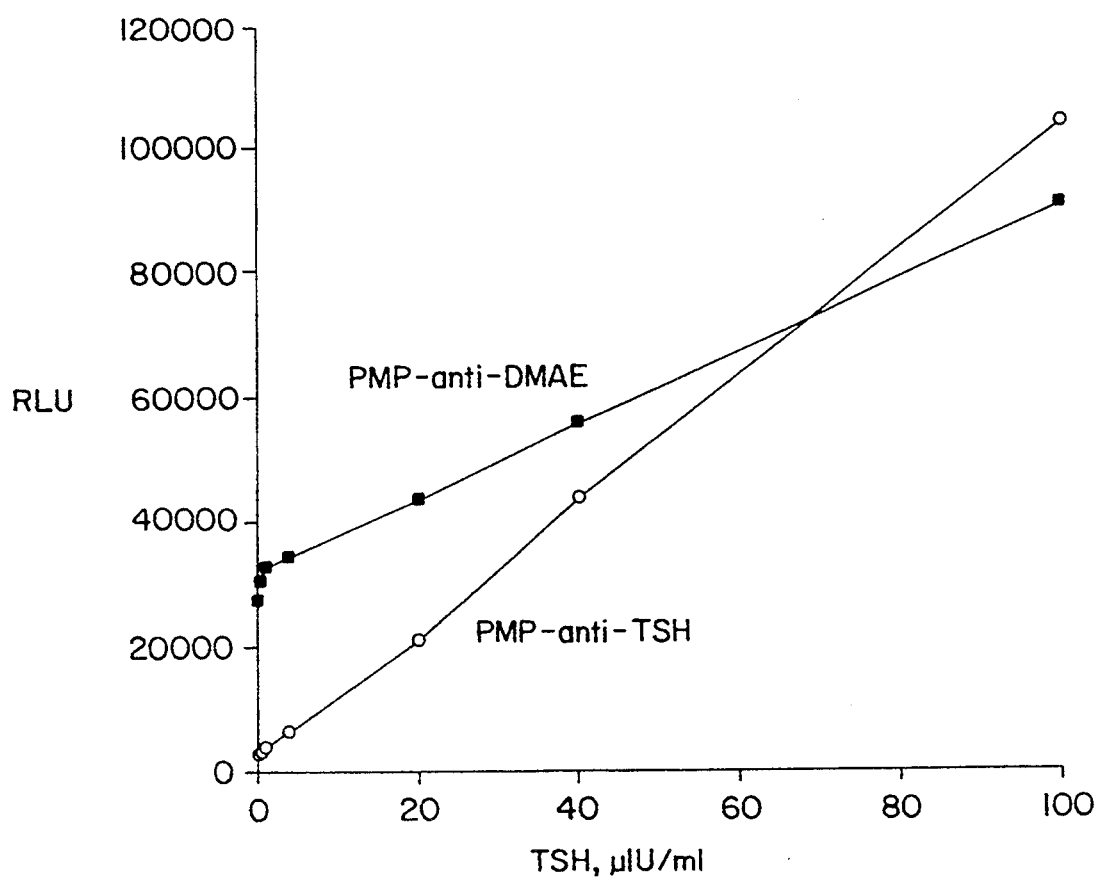
FIG. 11 shows the results obtained in the assay for TSH using the present invention which utilizing either a capture with an immobilized anti-label or an immobilized anti-analyte.

The standard curves are shown in FIG. 11. The signal at zero dose is relatively high with PBP-anti-DMAE as the capture antibody, since the tracer was not affinity purified. Capture with PMP-anti-TSH (11A8) gave a low zero dose signal because the labeled, but inactive tracer was not captured. It is thus obvious that affinity purification of the tracer will greatly improve the assay with PMP-anti-DMAE and may also improve the assay with PMP-anti-TSH.

What is claimed is:

1. A binding assay procedure for determination of an analyte, such procedure being conducted in one container, by
   a. mixing the solution containing the analyte with a labeled specific binder which binds to a first binding site on the analyte to form an analyte-labeled specific binder complex,
   b. contacting the solution from step a with one or more materials which comprise
      1. a reagent which contains an insoluble material to which is attached an analyte derivative or an analyte mimic that binds the labeled specific binder that had not bound analyte to form an insoluble material—labeled specific binder complex and
      2. a reagent that contains a second binder which binds to one portion of the analyte-labeled specific binder complex, such second binder being bound to a solid phase, such that the insoluble material, by binding to the labeled specific binder that had not bound analyte, inhibits the binding of the unreacted labeled specific binder to the solid phase, c. measuring the label associated with the solid phase wherein said label is measured: (i) after separation of said solid phase from said insoluble material and the liquid components of the reaction mixture, (ii) without separation of said solid phase from said insoluble material and the liquid components of the reaction mixture in the case of a pseudohomogeneous assay format, or (iii) without separation of said solid phase from said insoluble material and the liquid components of the reaction mixture in the case of a sensor assay format and d. determining the amount of analyte by comparing the amount of said label measured to that in a reference solution.

2. A binding assay procedure of claim 1 which is an immunoassay, a gene probe assay, a protein binding assay, a receptor assay, a free hormone assay, or a free drug assay.

3. A binding assay of claim 1 wherein the analyte contains one epitope.

4. A binding assay of claim 1 wherein the analyte contains two or more epitopes.

5. A binding assay of claim 1 wherein the insoluble material is selected from controlled pore glass, polymer particles, latex particles, cross-linked dextran or an extended surface.

6. A binding assay of claim 1 in which the solid phase is paramagnetic particles or an extended surface.

7. A binding assay of claim 1 which, in addition, includes a step wherein the solid phase and attached labeled material is separated from the reaction mixture and washed before determining the amount of label attached to the solid phase.

8. A binding assay of claim 7 in which the technique for separating the solid phase involves magnetic separation or centrifugation.

9. A binding assay of claim 1 in which the label is an acridinium ester or an enzyme.

10. A binding assay procedure for determination of an analyte, such procedure being conducted in one container, by a. mixing the solution containing the analytes with an acridinium ester labeled specific binder which binds to a first binding site on the analyte to form an analyte-labeled specific binder complex, b. contacting the solution from step a with one or more materials which comprise
   1. a reagent which contains controlled pore glass to which is bound an analyte derivative or an analyte mimic that binds the labeled specific binder that had not bound analyte to form a controlled pore glass-labeled specific binder complex and
   2. a reagent that contains a second binder which binds to one portion of the analyte-labeled specific binder complex, such second binder being bound to paramagnetic particles, such that the controlled pore glass, by binding to the labeled specific binder that had not bound analyte inhibits the binding of the unreacted labeled specific binder to the paramagnetic particles, c. measuring said acridinium ester label associated with said paramagnetic particles after separation of said paramagnetic particles from said controlled pore glass and the liquid components of the reaction mixture, and d. determining the amount of analyte by comparing the amount of said acridinium ester measured to that in a reference solution.

11. A binding assay of claim 1 in which a sensor replaces the solid phase, and the label associated with said sensor is measured.

* * * * *